(12) United States Patent
Rohkohl et al.

(10) Patent No.: US 8,768,045 B2
(45) Date of Patent: Jul. 1, 2014

(54) METHOD FOR ACQUIRING A 3D IMAGE DATASET FREED OF TRACES OF A METAL OBJECT

(75) Inventors: Christopher Rohkohl, Bochum (DE); Bernhard Scholz, Heroldsbach (DE)

(73) Assignee: Siemens Aktiengesellschaft, München (DE)

( * ) Notice: Subject to any disclaimer, the term of this patent is extended or adjusted under 35 U.S.C. 154(b) by 57 days.

(21) Appl. No.: 13/420,706

(22) Filed: Mar. 15, 2012

(65) Prior Publication Data

US 2012/0237115 A1      Sep. 20, 2012

(30) Foreign Application Priority Data

Mar. 17, 2011    (DE) .......................... 10 2011 005 715

(51) Int. Cl.
*G06K 9/00*    (2006.01)
(52) U.S. Cl.
USPC ............... 382/154; 382/131; 382/165; 378/4; 378/97
(58) Field of Classification Search
CPC ....... G06T 17/00; G06T 19/00; G06T 7/0081; A61B 6/5258
USPC .................. 382/131, 154; 345/626; 378/4, 97
See application file for complete search history.

(56) References Cited

U.S. PATENT DOCUMENTS

| | | | | |
|---|---|---|---|---|
| 5,672,877 A * | 9/1997 | Liebig et al. | ............. | 250/363.04 |
| 6,341,152 B1 * | 1/2002 | Sugihara | ............. | 378/4 |
| 6,650,724 B2 * | 11/2003 | Strobel | ............. | 378/4 |
| 7,148,903 B2 | 12/2006 | Brunner et al. | | |
| 7,356,174 B2 * | 4/2008 | Leue et al. | ............. | 382/131 |
| 7,627,079 B2 * | 12/2009 | Boone | ............. | 378/4 |
| 8,027,526 B2 * | 9/2011 | Boese et al. | ............. | 382/131 |
| 2006/0171578 A1 * | 8/2006 | Novak | ............. | 382/131 |
| 2008/0247624 A1 * | 10/2008 | Scholz | ............. | 382/131 |
| 2008/0292055 A1 * | 11/2008 | Boone | ............. | 378/97 |
| 2009/0274354 A1 * | 11/2009 | Ng et al. | ............. | 382/131 |
| 2011/0243398 A1 * | 10/2011 | Suzuki et al. | ............. | 382/118 |
| 2012/0163687 A1 * | 6/2012 | Plakas et al. | ............. | 382/131 |
| 2012/0230583 A1 * | 9/2012 | Inoshita | ............. | 382/165 |

FOREIGN PATENT DOCUMENTS

| | | |
|---|---|---|
| DE | 10306016 A1 | 9/2004 |
| DE | 102007016319 A1 | 10/2008 |
| DE | 102008048716 A1 | 12/2009 |

OTHER PUBLICATIONS

Reduction of CT artifacts caused by metallic implants Kalender et al.; Radiology vol. 164, No. 2, pp. 576-577; Radiology; Magazine; 1987.

(Continued)

*Primary Examiner* — Vu Le
*Assistant Examiner* — Aklilu Woldemariam

(57) ABSTRACT

An interpolation of data values is performed during the acquisition of a 3D image dataset which is free of traces of a metal object imaged in the underlying 2D image datasets. A target function is defined into which data values of the 3D image dataset that are dependent on said substitute data values are incorporated following preprocessing. The substitute data values are then varied iteratively until the value of the target function satisfies a predetermined criterion. Residual artifacts that still persist following the interpolation can thus be effectively reduced.

8 Claims, 3 Drawing Sheets

(56) References Cited

OTHER PUBLICATIONS

T. Hinderling, P. Rüegsegger, M. Anliker, C. Dietschi; Computed tomography reconstruction from hollow projections: an application to in vivo evaluation of artificial hip joints Hinderling et al.; J Comput Assist Tomogr. Feb. 1979;3(1) pp. 52-57.; Others; 1979.

D. Felsenberg, W. Kalender, R. Sokiranski, J. Ebersberger, R. Krämer; Reduktion von Metallartefakten in der Computertomographie: Klinische Erfahrungen und Ergebnisse Electromedica, 56(3), pp. 97-104, 1988; Others; 1988.

A.H. Mahnken et al.; A new algorithm for metal artifact reduction in computed tomography: in vitro and in vivo evaluation after total hip replacement Invest Radiol. Dec. 2003;38(12):pp. 769-775; Others; 2003.

Jan Müner and Thorsten M. Buzug; Intersection Line Length Normalization in CT Projection Data Buchreihen Informatik aktuell Buch Bildverarbeitung für die Medizin 2008 Verlag Springer Berlin Heidelberg Part 4, pp. 77-81; Book; 2008.

Jan Müller and Thorsten M. Buzug; Spurious structures created by interpolation-based CT metal artifact reduction Medical Imaging 2009: Physics of Medical Imaging. Edited by Samei, Ehsan; Hsieh, Jiang. Proceedings of the SPIE, vol. 7258 (2009)., pp. 72581Y-72581Y-8 (2009).; Others; 2009.

Esther Meyer et al. Normalized Metal Artifact Reduction (NMAR) in Computed Tomography Nuclear Science Symposium Conference Record (NSS/MIC), 2009 IEEE, pp. 3251-3255 M09-206; Others; 2009.

B. De Man et al. Reduction of metal streak artifacts in x-ray computed tomography using a transmission maximum a posteriori algorithm IEEE Transactions on Nuclear Science, vol. 47, nr. 3, 2000, pp. 977-981.; Others; 2000.

R.C. Gonzalez et al.: Digital Image Processing—Second Edition. Prentice-Hall, 2002, p. 567,568,598-600, 613-615; Others; 2002.

\* cited by examiner

METHOD FOR ACQUIRING A 3D IMAGE DATASET FREED OF TRACES OF A METAL OBJECT

CROSS REFERENCE TO RELATED APPLICATIONS

This application claims priority of German application No. 10 2011 005 715.3 filed Mar. 17, 2011, which is incorporated by reference herein in its entirety.

FIELD OF INVENTION

The invention relates to a method for acquiring a 3D image dataset from a plurality of 2D image datasets acquired with the aid of an X-ray image recording device. Such a method is known for example from DE 10 2007 016 319 A1.

BACKGROUND OF INVENTION

The 3D image dataset is intended to be free in particular of traces of at least one metal object imaged in at least some of the 2D image datasets. Such traces, customarily also referred to as artifacts, occur due to the way in which the 3D image dataset is calculated from 2D image datasets. In 2D image datasets, grayscale values are assigned to picture elements (pixels) in a two-dimensional image raster which correspond to pixels of e.g. an X-ray beam detector. In a 3D image dataset, grayscale values are assigned to voxels that are defined in the space filled by the image object, the grayscale values reflecting the extent to which the image object attenuates X-radiation in the region of the said voxel. The 3D image datasets are generated from the 2D image datasets by means of a 3D reconstruction operating e.g. according to the filtered back-projection principle. In this case it has been assumed that in each 2D image dataset the three-dimensional space has been projected in a specific manner into the image plane, making a back-projection possible. In a 2D X-ray image, a metal object leads to a particularly low grayscale value. In the back-projection of such a metal object on the basis of line integrals this is reflected not only in the fact that the grayscale values associated with the voxels which are occupied by the metal object also become correspondingly extremal, but also in that streak-shaped artifacts are present due to the back-projection principle. Said artifacts, also in the voxels which are occupied by soft parts of a typical image object, impede the interpretation of the reconstructed volume.

For this reason an attempt is made to remove not only the metal objects by computational means, but in particular also the associated artifacts. This is best accomplished by equalizing the corresponding grayscale values associated with the metal object already in the underlying 2D image datasets, in other words by eliminating the traces of the metal object. Said equalization is achieved in particular through interpolation. It is explicitly disclosed in DE 10 2007 016 319 A1, for example, according to which formula such an interpolation can be calculated. The interpolation causes substitute grayscale values (substitute data values) to be determined for individual pixels in the 2D image datasets. Outside of a specific region for the metal object, however, the 2D image datasets are preserved. A preprocessed 3D image dataset can then be generated on the basis of the thus preprocessed 2D image datasets.

It is evident, however, that such an interpolation and subsequent filtered back-projection (e.g. according to Feldkamp) nonetheless do not provide an assurance that the preprocessed 3D image dataset will be artifact-free.

DE 10 2007 016 319 A1 describes that such artifacts manifest themselves in the form of specific extrema in the grayscale values, so that by smoothing large gradients following the completion of the preprocessing it is possible to obtain a definitive three-dimensional reconstruction of the image object.

However, simply smoothing the large gradients on the basis of grayscale values assigned to pixels in their vicinity may lead to the loss of associated image information relating to the soft parts in the region of said large gradients which would otherwise be available.

SUMMARY OF INVENTION

It is therefore the object of the invention to provide a method for acquiring a 3D image dataset which is artifact-free to a greater extent, without image information being lost.

The object is achieved by a method having the features recited in the claims.

According to the invention, therefore, a value of a target function is determined from data values of the preprocessed 3D image dataset that are dependent on the substitute data values, and the substitute data values are iteratively varied until the value of the target function satisfies a predetermined criterion.

The invention is based on the knowledge that in an interpolation dependencies exist between the results of the interpolation (the substitute data values) and other data values. Whereas according to DE 10 2007 016 319 A1 the gradients are smoothed directly, that is to say the data values that are dependent on the substitute data values are smoothed directly, without recourse to the substitute data values, in the present case the cause of the artifacts is combated, i.e. the substitute data values are optimized with the aim of minimizing the artifacts. This can be realized exceptionally well given suitable choice of the target function and appropriate predetermined criterion associated therewith.

The former knowledge that artifacts in particular can be identified by especially large gradients can be used to the effect that the value for the target function is determined through calculation of a gradient (or in particular a plurality of gradients) of data values of the preprocessed 3D image dataset. Accordingly the target function thus includes such a gradient in its formula, preferably even a whole sum over such gradients using a plurality of different summation elements.

In the course of the preprocessing it is possible to proceed from the point reached by existing knowledge. In particular the teaching from DE 10 2007 016 319 A1 except for the final step of smoothing gradients in the course of the preprocessing can also be performed in the method according to the invention. Thus, in the method according to the invention the interpolation is accordingly performed preferably in respect of the data values from the 2D image datasets, and the substitute data values are grayscale values in 2D image datasets calculated by means of the interpolation. It is therefore advantageous if the interpolation is performed in respect of the 2D image datasets so that traces of the metal object will already have been removed to a large extent prior to the back-projection and then the artifacts will already no longer be so pronounced in the preprocessed 3D image dataset. The interpolation is performed, as likewise known per se, in each case in respect of an image region which is identified according to a predetermined method as defined by a metal object. Accordingly the interpolation preferably takes place in a delimited region, the boundaries requiring to be suitably drawn. In this case the important point is that the boundaries are not drawn too widely so that valuable image information is lost as a result of the interpolation; on the other hand the boundaries must be drawn as precisely as possible around the metal object so that the artifacts will be effectively reduced. Preferably, therefore, the respective image region is initially determined on a provisional basis, and following an interpolation a differential image dataset is determined into which the differences of data values of the 2D image dataset not yet subjected to the interpolation on the one hand, and of the 2D image dataset following interpolation on the other hand, are incorporated. A correction of the provisional image region is then carried out on the basis of the differential image dataset.

The use of such a differential image is likewise the subject matter of DE 10 2007 016 319 A1. From said publication it is also known that the differential image dataset is determined and the image region corrected iteratively in the predetermined method, in particular until a predetermined criterion is satisfied. This optimization of the image region that is to be selected ensures to a particular degree that the preprocessed 3D image dataset will already have relatively few artifacts, with the result that the method based on the target function as cited in claim 1 can particularly effectively eliminate any residual artifacts.

In a preferred embodiment variant of the invention in which the interpolation takes place in respect of the 2D image datasets, a segmentation step is performed on the basis of the 3D image dataset. The image region is then determined or specified based on the result of the segmentation. The segmentation entails a comparison of a plurality of threshold values with the grayscale values of the 3D image dataset and, on the basis of the threshold values or the thus formed intervals, assignment of the grayscale values to specific groups, wherein said groups are then assigned specific grayscale values. In the simplest case a binary dataset is generated in which the metal object is assigned a grayscale value of 1 (or 256) and the region not filled by metal is assigned a grayscale value of 0. The image region can furthermore be specified for any 2D image dataset whenever such a binary image dataset is subjected to a so-called forward projection, i.e. when it is calculated how a 2D binary image will appear given the same projection direction as defined for the associated 2D image dataset. The projection direction is typically determined in that the X-radiation source of the X-ray image recording device is located in a certain position, while the X-radiation detector assumes an associated position. If, for example, the plurality of 2D image datasets are recorded by successive rotation of an X-ray C-arm, each angular position corresponds to a projection. A corresponding forward projection can then be calculated from a 3D image dataset. Going beyond what is disclosed in DE 2007 016 319 A1, a multi-stage segmentation is preferably performed: Firstly, a threshold value criterion is applied to the 3D image dataset. In this case, however, it can happen that edge zones in the 3D image dataset will not be adequately registered if an unsuitable choice of the threshold value is made. This can be corrected by incorporating neighboring areas of self-contained zones (self-contained in the geometrical sense) into said self-contained zones in accordance with a predetermined rule. Thus, the metal object can be registered initially only just within its actual borders according to the threshold value criterion and then the boundaries can be successively widened. This can be carried out using locally different boundaries. This multistage segmentation ensures a particularly precise identification of the metal object zone.

BRIEF DESCRIPTION OF THE DRAWINGS

A preferred embodiment variant of the invention is described in more detail below with reference to the drawing, in which.

DETAILED DESCRIPTION OF INVENTION

Figure 1:
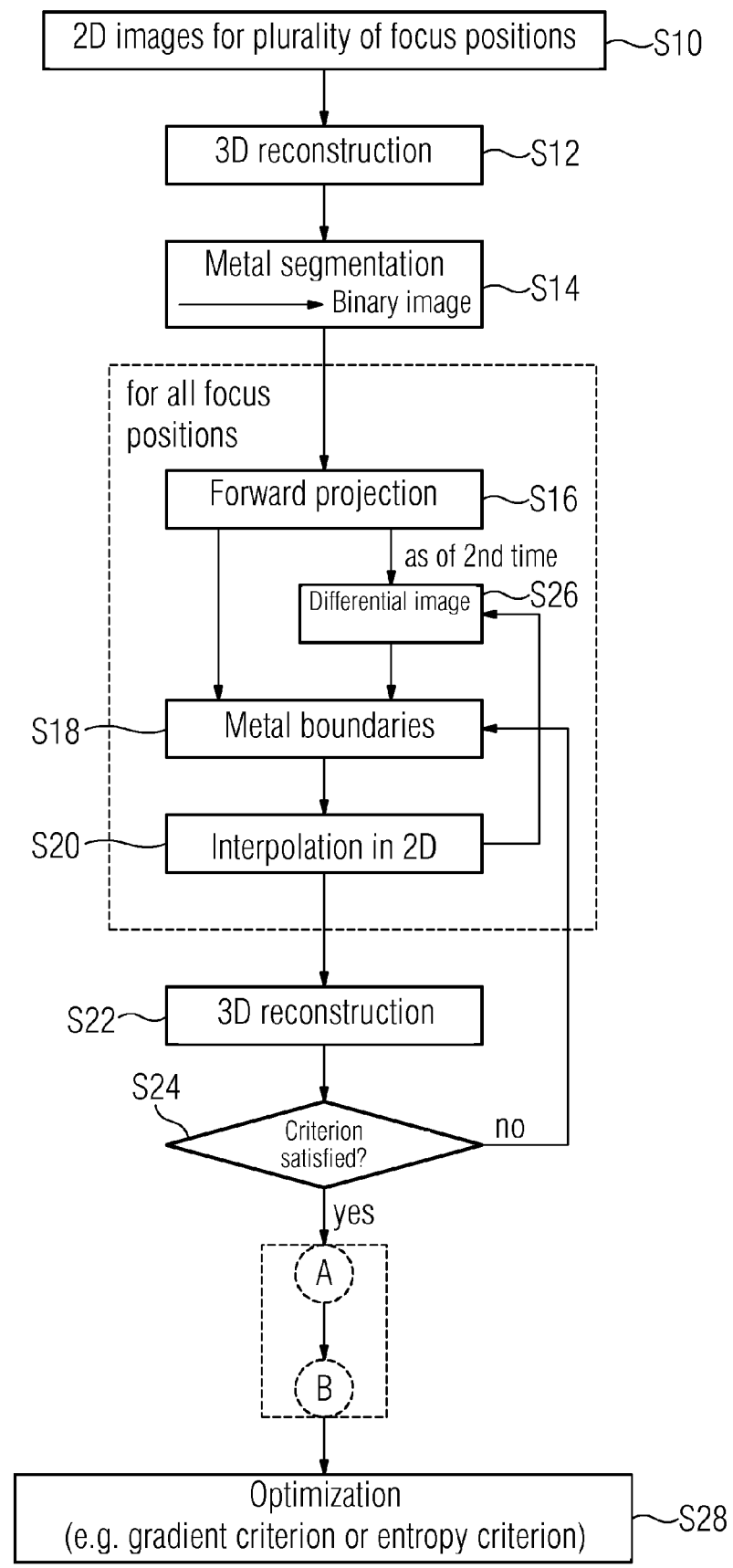
FIG. 1 is a flowchart serving to explain an embodiment variant of the method according to the invention.

The method according to the invention proceeds on the basis that an image object which is an arbitrary physiological body, although preferably an animal or human patient, and which somewhere contains or wears an element made of metal (metal object) is imaged with the aid of an X-ray image recording device. The X-ray image recording device can be an X-ray angiography system, for example. It is assumed that 2-dimensional X-ray images can be acquired with the aid of the X-ray image recording device, typically in that an X-radiation source transmits X-rays through the image object to an X-radiation detector whose measured values correspond as grayscale values to the pixels of the 2D image.

According to step S10 this acquisition of 2D images is performed for a plurality of focus positions. In this case the focus is the real X-ray source, in other words the origin of X-radiation which is punctiform in an X-ray source. The X-ray image recording device therefore permits the X-radiation source (and in particular also the X-radiation detector) to move such that a plurality of so-called projections are acquired if the individual 2D images are considered as projections of the image object from the respective focus position onto the plane of the X-radiation detector.

A 3D reconstruction according to step S12 can be calculated from a plurality of such projections, e.g. in accordance with what is known as the Feldkamp method (filtered back-projection), resulting in a 3D image dataset.

The metal object is thus a disruptive element in the individual 2D X-ray images due to the fact that it (for example) leads to particularly high grayscale values in a projection. As a result of the filtered back-projection these high grayscale values cause artifacts to be produced in the 3D image dataset. The object of the present method is to eliminate said artifacts to the greatest extent possible.

Firstly, a segmentation is performed in step S14 in respect of the 3D image dataset to the effect that areas of the image object that are occupied by metal are assigned a "1", and the other areas a "0". Such a binary image is obtained by initially specifying a threshold value and considering all voxels in which the associated grayscale values are above said threshold value as filled by metal. In the present case the aim is to perform the segmentation in a plurality of stages, the voxels accordingly being recorded initially as "seed points" with the aid of the threshold value criterion and moreover for a so-called "connected threshold segmentation". In a connected threshold segmentation a lower and an upper range value are specified. All voxels which are connected with the initially recorded voxels and in which the grayscale values lie in the cited value range between the lower and upper range values are added to the metal, i.e. saved as a segmented volume region.

In the present case the aim is in particular also to adjust the parameters regionally, which can be realized in a plurality of stages in the course of a segmentation. The regional adjustment of such parameters, for instance the lower and upper range value, is known per se.

After a binary image, in other words a 3D image dataset in which the individual voxels are assigned either a "1" or a "0", has thus been generated in step S14, the aim is now to ensure that the excessive grayscale values are no longer present in the 2D image datasets, i.e. the traces of the metal are to be eliminated. Accordingly, the following steps, as known per se from DE 10 2007 016 319 A1, are performed for all focus positions for which a 2D image dataset has been acquired: According to step S16, a forward projection is calculated from the binary image, in other words it is calculated how, given the attenuation according to the binary image, a 2D X-ray image would appear, and moreover an image such as would be recorded at the same focus position as one of the 2D images acquired in step S10. On the basis of this forward projection calculated in step S16 it is then possible in step S18 to determine the boundaries indicated by the metal in the cited projection. Next, the associated 2D image can then be interpolated, whereby the interpolation in relation to the metal boundaries obtained in step S18 is performed in step S20. It is pointed out that the metal boundaries are determined on the basis of the forward projection, which is the forward projection of a binary image. The interpolation, on the other hand, is then performed in the 2D images acquired in step S10.

After this interpolation has been calculated for all focus positions it is possible once again, namely in step S22, to calculate a 3D reconstruction.

Certain criteria can now be applied to the thus acquired 3D image dataset—see step S24—in order to test whether the 3D reconstruction from step S22 fulfills a specific quality standard. With regard to said criteria, reference is made specifically to DE 10 2007 016 319 A1. Let it be cited by way of example that the extent of gradients in the 3D image dataset can be calculated, and if the gradients exceed a threshold value the criterion can be regarded as not satisfied.

Let it be assumed in the present case that the criterion is initially regarded as not satisfied. A return is then made to step S18. As a result of an interpolation having been calculated in step S20, a 2D image dataset is available in which the metal has been computationally eliminated. Accordingly, from said 2D image dataset and the forward projection acquired in step S16 it is possible, as of the second time of passing through steps S18, S20 and S22, to calculate a differential image in step S26. This is explained in detail in DE 10 2007 016 319 A1. As a result of the differential image the metal stands out in much sharper contrast, enabling the metal boundaries to be drawn more precisely in step S18 than previously. An interpolation according to step S20 can then be performed once again and a 3D reconstruction calculated in step S22 if the interpolation in 2D image datasets is available for all focus positions. The iterative loop can relate to one focus position in each case, although preferably it relates to all focus positions. Where necessary step S14 can even be repeated a further time if a 3D reconstruction is acquired from differential images and a metal segmentation is then made possible.

In the present case let it be assumed that the criterion inserted in step S24 is eventually satisfied. Optionally a pass can now be made through the step sequence (from "A" to "B") shown in FIG. 2, a discussion of which will be deferred until later in the description. In any event the result of this step sequence is likewise a 3D reconstruction, so either the 3D reconstruction obtained from the last pass through step S22 can be used directly or the 3D reconstruction obtained as a result of the step sequence according to FIG. 2 can be used.

Figure 3:
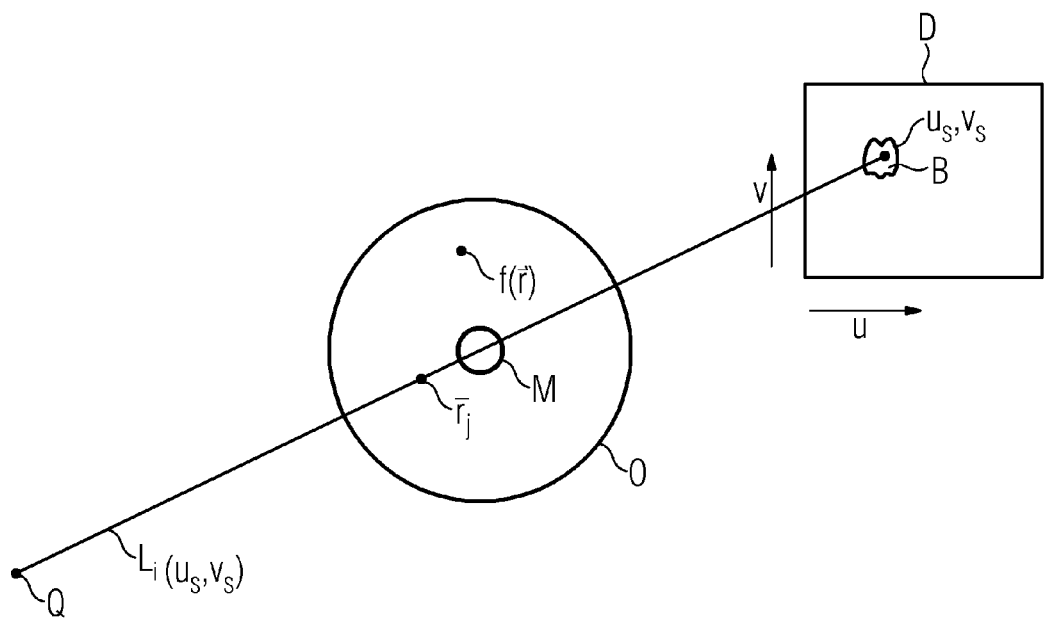
FIG. 3 shows a perspective view serving to explain mathematical variables which occur in a target function playing a significant role in the invention.

It has now been assumed that by means of the measures passed through, in other words at least steps S10 to S26, it has been ensured that the 3D image dataset is low in artifacts, i.e. that metal objects no longer have an excessively disruptive impact in image regions outside of the metal object. In step S28 an optimization is now performed with the aim of removing the artifacts to an even greater extent. In the course of the optimization a gradient criterion or an entropy criterion or some other criterion can be applied. In the present case the optimization based on the gradient criterion is described in more detail:

It has been assumed that the geometric conditions according to FIG. 3 apply at an i-th focus position (projection i). X-rays originating from the X-radiation source Q and passing through the line $L_{i\,(us,\,vs)}$ are incident onto a point $u_s$, $v_s$ in the plane of an X-radiation detector D. Let the image object O include a metal object M. In the 3D image dataset, voxels to which the location $\vec{r}$ can be assigned are assigned the values $f(\vec{r})$ as grayscale values. There is now a set of such location vectors $r_j$ which lie on the line $L_{i(us,\,vs)}$.

In the present case let the following function now be calculated:

$$Z(\underline{s}) = \sum_i \sum_{(u_s,v_s)} \sum_{r_j \in Li;(u_s,u_s)} |\vec{\nabla} f(\vec{r}, s)|$$

Here, $\underline{s}$ is the vector of all the interpolation data, in other words of all data values (grayscale values) that have been specified as a result of the interpolation. In the simplest case they are those grayscale values which have replaced the former data values in the determined region B. This data, e.g. data determined during the last pass through step S20 with omission of the partial method according to FIG. 2, is modified once again in the course of the optimization in step S28. Moreover, the target function $Z(\underline{s})$ can be minimized in an algorithm known per se. Known algorithms are e.g. Newton's method, the gradient descent method (in which case said gradient would then relate to the target function itself), Powell's method, etc. The gradient $|\vec{\nabla} f(\vec{r},\underline{s})|$ emerging in the target function $Z(\underline{s})$ is an overall gradient at the function $f(\vec{r})$ in three spatial directions. Said gradient indicates the extent to which the metal object M is reflected in the form of rays or streaks in the 3D image dataset. Accordingly, the streaks, which are the disruptive artifacts, can be effectively reduced by minimizing the sum over said gradients. The optimal interpolation vector $\underline{s}$ that is obtained at the end is therefore such that the traces of the metal object M in the 3D image dataset have been optimally eliminated.

Figure 2:
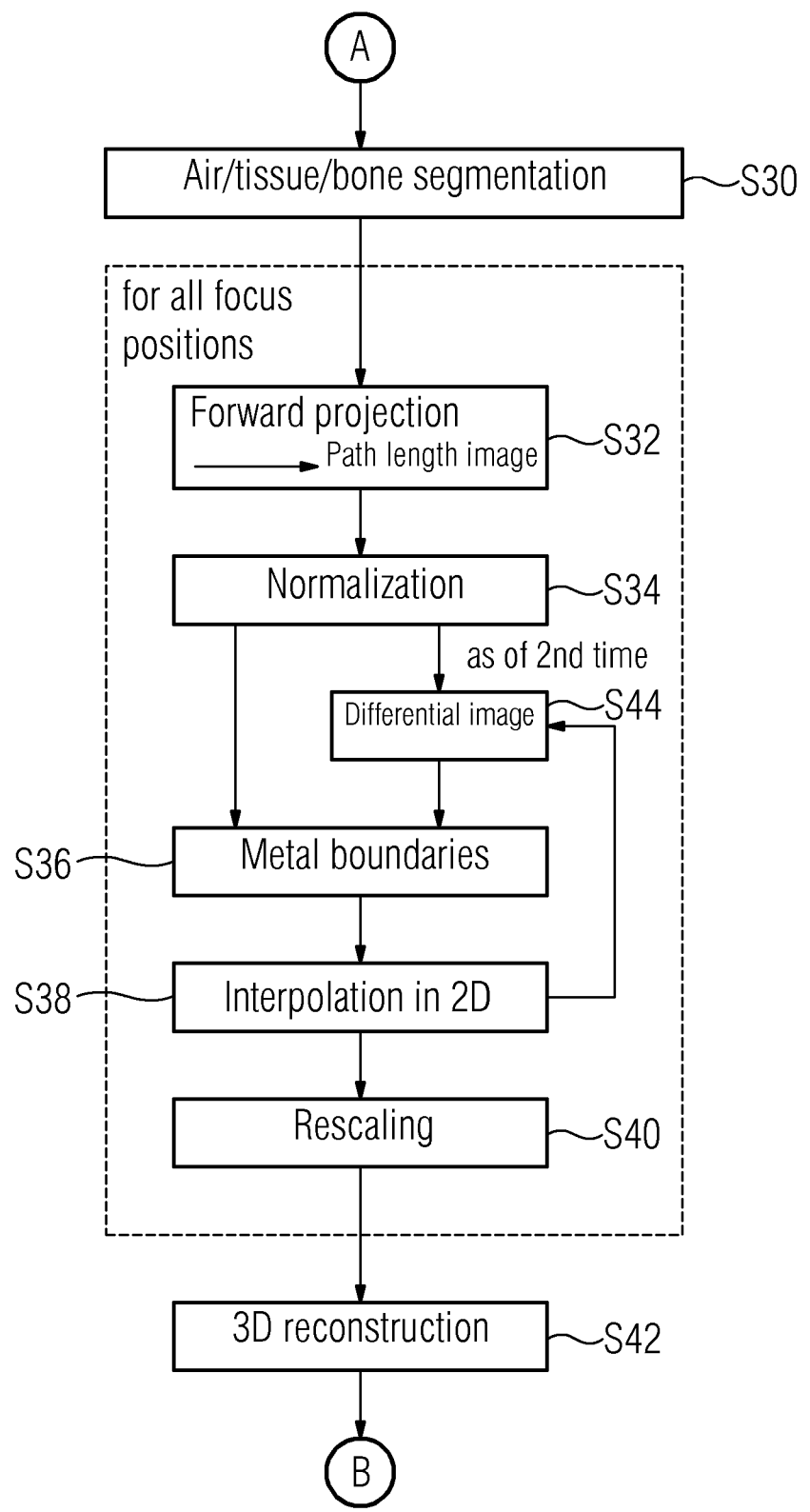
FIG. 2 is a flowchart serving to explain a partial method which can optionally be applied within the method explained with reference to FIG. 1.

In order to refine the described method, the steps according to FIG. 2 are additionally performed between steps S24 and S28. In step S30 the 3D image dataset is subjected to a different type of segmentation. Through the specification of particular grayscale value ranges the grayscale values can be assigned information indicating whether said values correspond to the imaging of air, tissue or bone. (The segmentation in respect of metal has of course already been completed in step S14.) In the manner of steps S16 to S20 as well as step S26, a forward projection is now calculated again for all focus positions in step S32. This forward projection is somewhat different from the forward projection from step S16: As a result of the segmentation air, tissue and bone are incorporated in it with weighting factors that correspond to the degree to which air, tissue and bone in each case attenuate X-radiation. The image thus obtained is referred to as a "path length image". Said path length image can then be used in step S34 to normalize the 2D image datasets that were interpolated during the last pass through step S20 so that said 2D image datasets are available in a version that is comparable with the path length image. The metal boundaries can then be identified in step S36 so that a further interpolation can be performed again in step S38 on the basis of the normalized 2D X-ray image datasets. If necessary, a differential image for the 2D image dataset obtained in step S34 can be calculated again here following the interpolation so that the metal boundaries can be determined once more in step S36 with even greater precision. After the last pass through step S38 a scaling can be performed in step S40 so that the 2D image datasets will again be available in a form permitting a 3D reconstruction in the following step S42.

After step S42 the optimization according to step S28 can then be performed as in other cases after steps S22 and S24, without substeps S30 to S42 being performed.

The partial method described here with reference to steps S30 to S42 is known per se and is described e.g. in the following publications:

1. J. Müller, T. M. Buzug, "Intersection Line Length Normalization in CT Projection Data", in Bildverarbeitung für die Medizin 2008 ("*Image processing for medicine* 2008"), Springer-Verlag Berlin Heidelberg
2. J. Müller, T. M. Buzug, "Spurious structures created by interpolation-based CT metal artifact reduction", SPIE Medical Imaging Proc., Vol. 7258, no. 1, pp. 1Y1-1Y8, 2009
3. Meyer E, Berger F, Raupach R, et al., "Normalized Metal Artifact Reduction (NMAR) in Computed Tomography", in: IEEE Medical Imaging Conference, Record 2009. Proceedings M09-206 October 2009, Orlando, Fla.

For further details relating to the partial method, the reader is referred to these publications.

In summary let it be stated that through the combination of multistage metal segmentation in step S14, the method known per se from DE 10 2007 016 319 A1, and optionally the partial method described with reference to FIG. 2, a 3D image dataset that already has very few artifacts is available which then makes the optimization according to step S28 which is at the center of the present description particularly efficient. The cited target function can appear differently than described above. For example, an entropy can be defined in relation to the individual 2D image datasets and it can then be brought about that the interpolation parameters s are chosen such that the entropy is as small as possible in terms of absolute amount.

The invention claimed is:

1. A method for acquiring a 3D image dataset, comprising:
    acquiring a plurality of 2D image datasets with a metal object imaged in at least some of the 2D image datasets using an X-ray image recording device;
    reconstructing an initial 3D image dataset from the 2D image datasets, wherein the initial 3D image includes artifacts comprising traces of the metal object;
    generating a preprocessed 3D image dataset from the initial 3D image datasets that is lower in artifacts by determining a plurality of substitute data values for data values associated with the metal object for the preprocessed 3D image dataset during the preprocessing by interpolating data values of the 2D image datasets;
    optimizing the substitute data values from the preprocessed 3D image dataset to further minimize artifacts by:
        determining a value of a target function from the preprocessed 3D image dataset that is dependent on the substitute data values;
        iteratively determining the substitute data values until the value of the target function satisfies a predetermined criterion; and
        reconstructing a further 3D image dataset that is free of traces of the metal object once the predetermined criterion is satisfied,
    wherein the value of the target function is determined by calculating a gradient of data values of the preprocessed 3D image dataset,
    eliminating residual artifacts in the preprocessed 3D image dataset by minimizing gradient in the target function,
    wherein the target function is defined as follows:

$$Z(\underline{s}) = \sum_i \sum_{(u_s, v_s)} \sum_{r_j \in Li;(u_s, u_s)} |\vec{\nabla} f(\vec{r}, \underline{s})|,$$

s is a vector of the interpolated data values
$(u_s, v_2)$ is a point in a plane of an X-radiation detector of the X-ray image recording device,
Li (us, vs) a line passing through X-rays originating from a X-radiation source of the X-ray image recording device,
$\vec{r}$ is a location of a voxel in the preprocessed 3D image dataset, and
$|\vec{\nabla} f(\vec{r}, \underline{s})|$ is the gradient in three spatial directions,
predetermined criterion is defined that the gradient does not exceed a threshold value.

2. The method as claimed in claim 1, wherein the substitute data values are grayscale values in the 2D image datasets.

3. The method as claimed in claim 1, wherein the interpolation is performed in an image region in the 2D image datasets defined by the metal object.

4. The method as claimed in claim 3,
    wherein the image region is provisionally determined from the initial 3D image dataset,
    wherein the interpolation is performed in the provisionally determined image region,
    wherein a differential image dataset is determined based on differences of data values of the 2D image datasets before and after the interpolation, and
    wherein the image region is corrected based on the differential image dataset.

5. The method as claimed in claim 4, wherein the image region is iteratively corrected based on the differential image dataset until a predetermined criterion is satisfied.

6. The method as claimed in claim 3, wherein the metal object is segmented prior to the interpolation and the image region is defined based on the segmentation.

7. The method as claimed in claim 6, wherein the segmentation is performed by steps of:
    applying a threshold value criterion to the initial 3D image dataset defining actual borders of the metal object, and
    incorporating neighboring areas of the actual borders of the metal object into the actual borders according to a predetermined rule.

8. The method as claimed in claim 1, wherein the optimization comprises applying a gradient criterion or an entropy criterion to the preprocessed 3D image dataset.

* * * * *